(12) United States Patent
Shartle et al.

(10) Patent No.: US 7,548,772 B2
(45) Date of Patent: *Jun. 16, 2009

(54) ELECTRICALLY-CONDUCTIVE PATTERNS FOR MONITORING THE FILLING OF MEDICAL DEVICES

(75) Inventors: Robert Justice Shartle, Livermore, CA (US); Timothy J. Ohara, San Ramon, CA (US); Mahyar Z. Kermani, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/417,344

(22) Filed: May 2, 2006

(65) Prior Publication Data
US 2006/0200021 A1 Sep. 7, 2006

Related U.S. Application Data

(60) Continuation of application No. 10/975,258, filed on Oct. 28, 2004, now Pat. No. 7,050,843, which is a continuation of application No. 10/678,342, filed on Oct. 3, 2003, now abandoned, which is a division of application No. 09/540,319, filed on Mar. 31, 2000, now abandoned.

(51) Int. Cl.
*A61B 5/00* (2006.01)
(52) U.S. Cl. ............... 600/345; 600/347; 204/409
(58) Field of Classification Search ................. None
See application file for complete search history.

(56) References Cited

U.S. PATENT DOCUMENTS

| | | | |
|---|---|---|---|
| 4,244,125 A | 1/1981 | Corey | |
| 4,545,382 A | 10/1985 | Higgins et al. | |
| 4,940,945 A | 7/1990 | Littlejohn et al. | |
| 5,264,103 A | 11/1993 | Yoshioka et al. | |
| 5,266,179 A | 11/1993 | Nankai et al. | |
| 5,366,609 A | 11/1994 | White et al. | |
| 5,437,999 A | 8/1995 | Diebold et al. | |
| 5,514,120 A | 5/1996 | Johnston et al. | |
| 5,642,015 A | 6/1997 | Whitehead et al. | |
| 5,728,446 A | 3/1998 | Johnston et al. | |
| 5,798,031 A | 8/1998 | Charlton et al. | |
| 5,997,817 A | 12/1999 | Crismore et al. | |
| 6,004,441 A | 12/1999 | Fujiwara et al. | |
| 6,071,391 A | 6/2000 | Gotoh et al. | |
| 6,156,173 A | 12/2000 | Gotoh et al. | |

(Continued)

FOREIGN PATENT DOCUMENTS

EP    0974840 B1    12/2002

(Continued)

OTHER PUBLICATIONS

G. Urban, et al., "Performance of Integrated Glucose and Lactate Thin-Film Microbiosensors for Clinical Analysers", Sensors and Actuators B, vol. 18-19, pp. 592-596, 1994.

(Continued)

*Primary Examiner*—Robert L Nasser

(57) ABSTRACT

A flexible diagnostic device has a measurement cell that is sandwiched between the conductive surfaces of two conductive-coated insulating layers. At least one of the conductive surfaces is scored with an insulating pattern, so that the flow of a conductive fluid sample into the cell can be monitored.

12 Claims, 7 Drawing Sheets

U.S. PATENT DOCUMENTS

| | | |
|---|---|---|
| 6,212,417 B1 | 4/2001 | Ikeda et al. |
| 6,258,229 B1 | 7/2001 | Winarta et al. |
| 6,287,451 B1 | 9/2001 | Winarta et al. |
| 6,299,757 B1 | 10/2001 | Feldman et al. |
| 6,338,790 B1 | 1/2002 | Feldman et al. |
| 6,461,496 B1 | 10/2002 | Feldman et al. |
| 6,503,381 B1 | 1/2003 | Gotoh et al. |
| 6,576,101 B1 | 6/2003 | Heller et al. |
| 6,576,461 B2 | 6/2003 | Heller et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |

FOREIGN PATENT DOCUMENTS

| | | | |
|---|---|---|---|
| RU | 2145081 C1 | 1/2000 | |
| RU | 2267131 C2 | 12/2005 | |
| WO | WO 95/22597 A1 | 8/1995 | |
| WO | WO 97/02487 A1 | 1/1997 | |
| WO | WO 97/18464 A1 | 5/1997 | |
| WO | WO 99/45387 A2 | 9/1999 | |
| WO | WO 99/45387 A3 | 9/1999 | |
| WO | 01/75438 | * 11/2001 | ................ 600/347 |

OTHER PUBLICATIONS

English translation of abstract and drawings of Russian Patent RU 2049991 issued Dec. 10, 1995, Gindilis A.L.

* cited by examiner

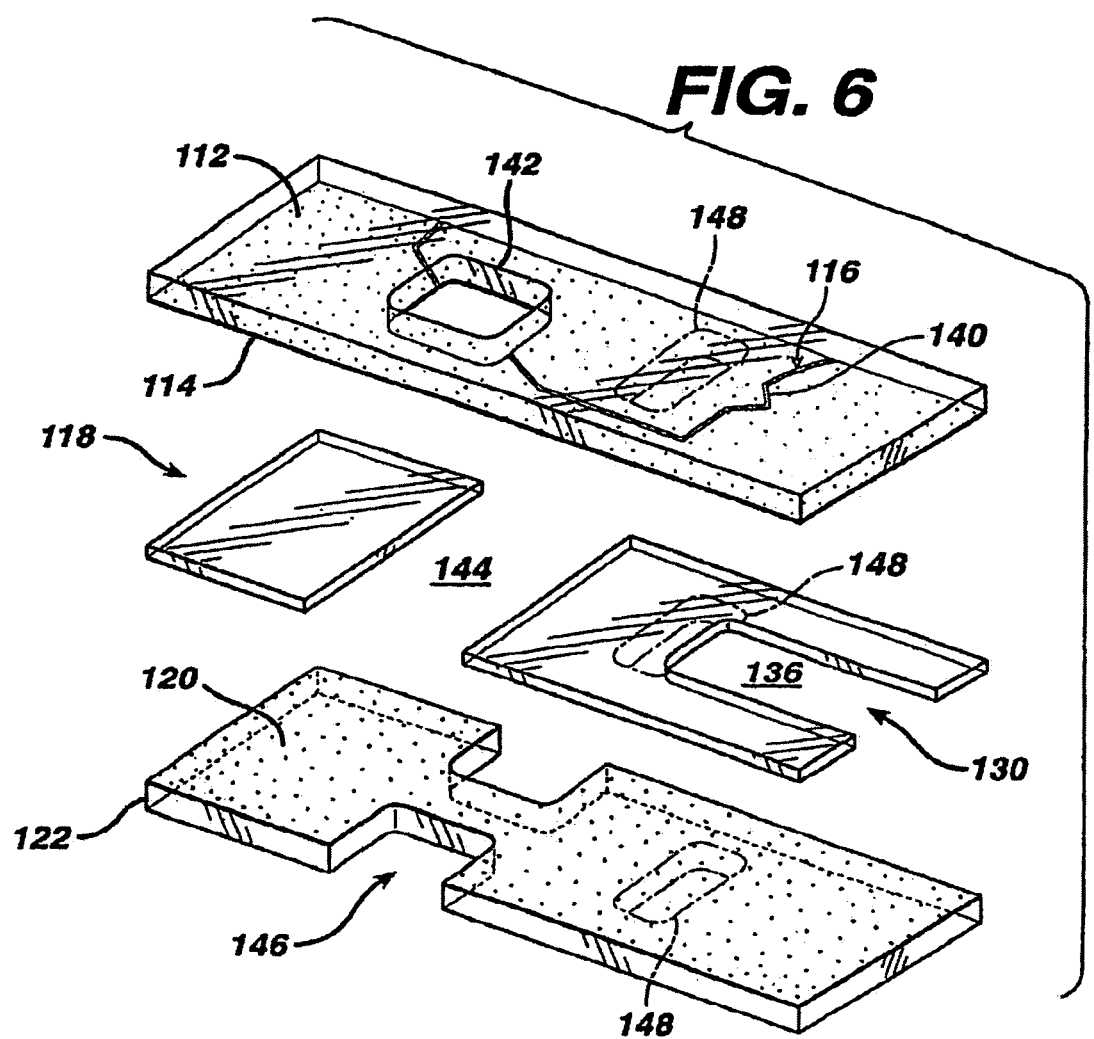

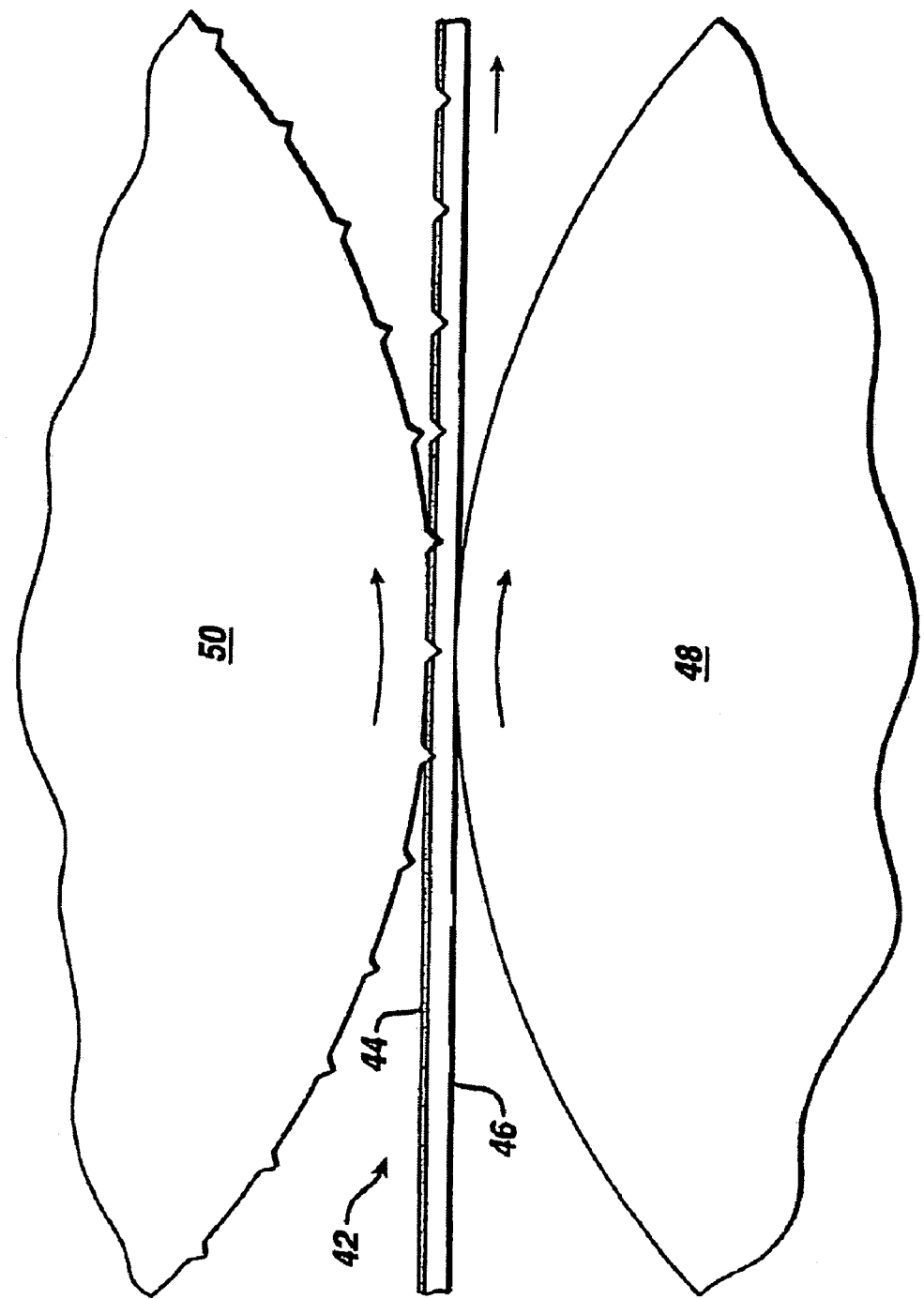

ELECTRICALLY-CONDUCTIVE PATTERNS FOR MONITORING THE FILLING OF MEDICAL DEVICES

This application is a continuation of U.S. application Ser. No. 10/975,258 filed Oct. 28, 2004, now U.S. Pat. No. 7,050,843; which is a continuation of U.S. application Ser. No. 10/678,342 filed Oct. 3, 2003, now abandoned; which is a divisional of U.S. application Ser. No. 09/540,319 filed Mar. 31, 2000, now abandoned; which are incorporated herein by reference and to which Applicants claim priority.

BACKGROUND OF THE INVENTION

1. Field of the Invention

This invention relates to a diagnostic device that has an insulating pattern scored into a conductive coating on the device to facilitate analytical measurements; more particularly, to monitor filling of the device.

2. Description of the Related Art

A variety of medical diagnostic procedures involve tests on biological fluids, such as blood, urine, or saliva, to determine an analyte concentration in the fluid. The procedures measure a variety of physical parameters—mechanical, optical, electrical, etc.,—of the biological fluid.

Among the analytes of greatest interest is glucose, and dry phase reagent strips incorporating enzyme-based compositions are used extensively in clinical laboratories, physicians' offices, hospitals, and homes to test samples of biological fluids for glucose concentration. In fact, reagent strips have become an everyday necessity for many of the nation's estimated 16 million people with diabetes. Since diabetes can cause dangerous anomalies in blood chemistry, it can contribute to vision loss, kidney failure, and other serious medical consequences. To minimize the risk of these consequences, most people with diabetes must test themselves periodically, then adjust their glucose concentration accordingly, for instance, through diet, exercise, and/or insulin injections. Some patients must test their blood glucose concentration as often as four times or more daily.

One type of glucose measurement system operates electrochemically, detecting the oxidation of blood glucose on a dry reagent strip. The reagent generally includes an enzyme, such as glucose oxidase or glucose dehydrogenase, and a redox mediator, such as ferrocene or ferricyanide. This type of measurement system is described in U.S. Pat. No. 4,224,125, issued on Sep. 23, 1980, to Nakamura et al.; and U.S. Pat. No. 4,545,382, issued on Oct. 8, 1985, to Higgins et al., incorporated herein by reference.

Hodges et al., WO 9718464 A1, published on May 22, 1997, discloses an electrochemical device for measuring blood glucose that includes two metallized polyethylene terephthalate (PET) layers sandwiching an adhesive-coated PET intermediate layer. The metallized layers constitute first and second electrodes, and a cutout in the adhesive-coated layer defines an electrochemical cell. The cell contains the reagent that reacts with the glucose in a blood sample. The device is elongated, and the sample is introduced at an inlet on one of the long sides.

Nakai et al., U.S. Pat. No. 5,266,179, issued on Nov. 30, 1993, discloses an electrochemical system for measuring blood glucose, in which the sample application time is determined by a resistance drop between a pair of electrodes to which a constant voltage was applied.

White et al., U.S. Pat. No. 5,366,609, issued on Nov. 22, 1994, describes the same principle of monitoring the resistance drop between the electrodes to determine the time at which blood was applied to a dry glucose reagent strip. In both patents, a constant voltage is applied between working and reference electrodes to track resistance changes that result from the introduction of a blood sample to a dry reagent strip.

Accurately determining an analyte concentration generally requires a sufficient supply of sample. Yoshioka et al., U.S. Pat. No. 5,264,103, issued on Nov. 23, 1993, discloses a biosensor for electrochemically measuring concentration of an analyte, such as glucose, in a biological fluid. An impedance change indicates that a sufficient supply of sample has been supplied to the sensor.

Littlejohn et al., U.S. Pat. No. 4,940,945, issued on Jul. 10, 1990, discloses a portable apparatus that can measure pH of a blood sample. The apparatus detects the presence of a sample in a cell by injecting a constant current between a fill electrode outside the sample chamber and one of two electrodes inside the chamber. When the impedance decreases by at least two orders of magnitude, the meter recognizes that sufficient sample has been provided and emits a beep. The fill electrode is then cut out of the circuit that includes the two electrodes inside the sample cell, and measurements are made potentiometrically.

Crismore et al., U.S. Pat. No. 5,997,817, issued on Dec. 7, 1999, discloses an electrochemical sensor strip that includes a window through which a user can determine visually whether enough sample has been applied to the strip.

None of the above references discloses a mechanism for monitoring the movement of a blood sample into (and through) an electrochemical cell.

SUMMARY OF THE INVENTION

This invention provides a medical diagnostic device for measuring an analyte concentration of an electrically conductive biological fluid. The device comprises a multilayer structure having a first layer and a second layer sandwiching an intermediate layer, a) the first and second layers each comprising an insulating sheet, having a conductive surface adjoining the intermediate layer, b) the intermediate layer being an insulating layer with a cutout, having a first end and a second end, which, together with the first and second layers, defines a flow channel to permit the sample to flow from the first end to the second end, c) the flow channel comprising
  (i) a dry reagent on the conductive surface of one of the layers, for reacting with the sample to yield a change in an electrical parameter that can be related to the analyte concentration of the fluid, and
  (ii) an electrochemical cell, within which the electrical parameter is measured, d) the conductive surface of one of the layers having a first insulating pattern scored into its conductive surface to divide the layer into two regions, insulated from each other, whereby sample that flows across the pattern provides a conductive path from the first end to the second end.

For convenience, we refer to "one of" the layers in the above description and the claims, but we do not intend that phrase to exclude "both" layers.

A method for preparing an electrically conductive pattern of the present invention comprises passing a web of a conductive-coated flexible insulator between a cutting die and anvil, in which the cutting die has a cutting element that is raised a height greater than the thickness of the conductive coating for scoring through preselected portions of the conductive coating.

The present invention provides a medical diagnostic device that can easily sense when an adequate sample of a conductive biological fluid has been introduced into the device, without relying on the vision of the user. When the device measures glucose concentration, the user generally has diabetes and is frequently vision-impaired. In another embodiment, the invention provides a method for preparing an element of the diagnostic device. The method is well adapted for a high-speed, continuous line production process.

BRIEF DESCRIPTION OF THE DRAWINGS

FIG. 6 is an exploded perspective view of an alternative embodiment of the device of FIG. 1.

FIG. 7 depicts an apparatus for practicing a method of the present invention.

DETAILED DESCRIPTION OF THE INVENTION

This invention relates to an electrochemical method of measuring an analyte concentration of an electrically conductive biological fluid. In the interest of brevity, the description below emphasizes amperometrically measuring glucose concentration in samples of whole blood; however, the person of ordinary skill in the medical diagnostics art will recognize how the description can be adapted to measure other analytes (such as cholesterol, ketone bodies, alcohol, etc.) in other fluids (such as saliva, urine, interstitial fluid, etc.)

The electrochemical (amperometric) method for measuring an analyte concentration in an aqueous sample involves placing the sample into an electrochemical cell that has at least two electrodes and an impedance that is suitable for the amperometric measurement. The analyte is allowed to react directly with an electrode or with a redox reagent to form an oxidizable (or reducible) substance in an amount that corresponds to the analyte concentration. The quantity of oxidizable (or reducible) substance is then determined electrochemically.

In order to obtain an accurate measurement of the substance, it is important to assure that sufficient sample is provided to the cell. For example, if the sample is insufficient, it can reduce the effective electrode area and give an incorrect result. Assurance that the sample is sufficient is provided by the device of this invention, shown in FIG. 1.

Figure 1:
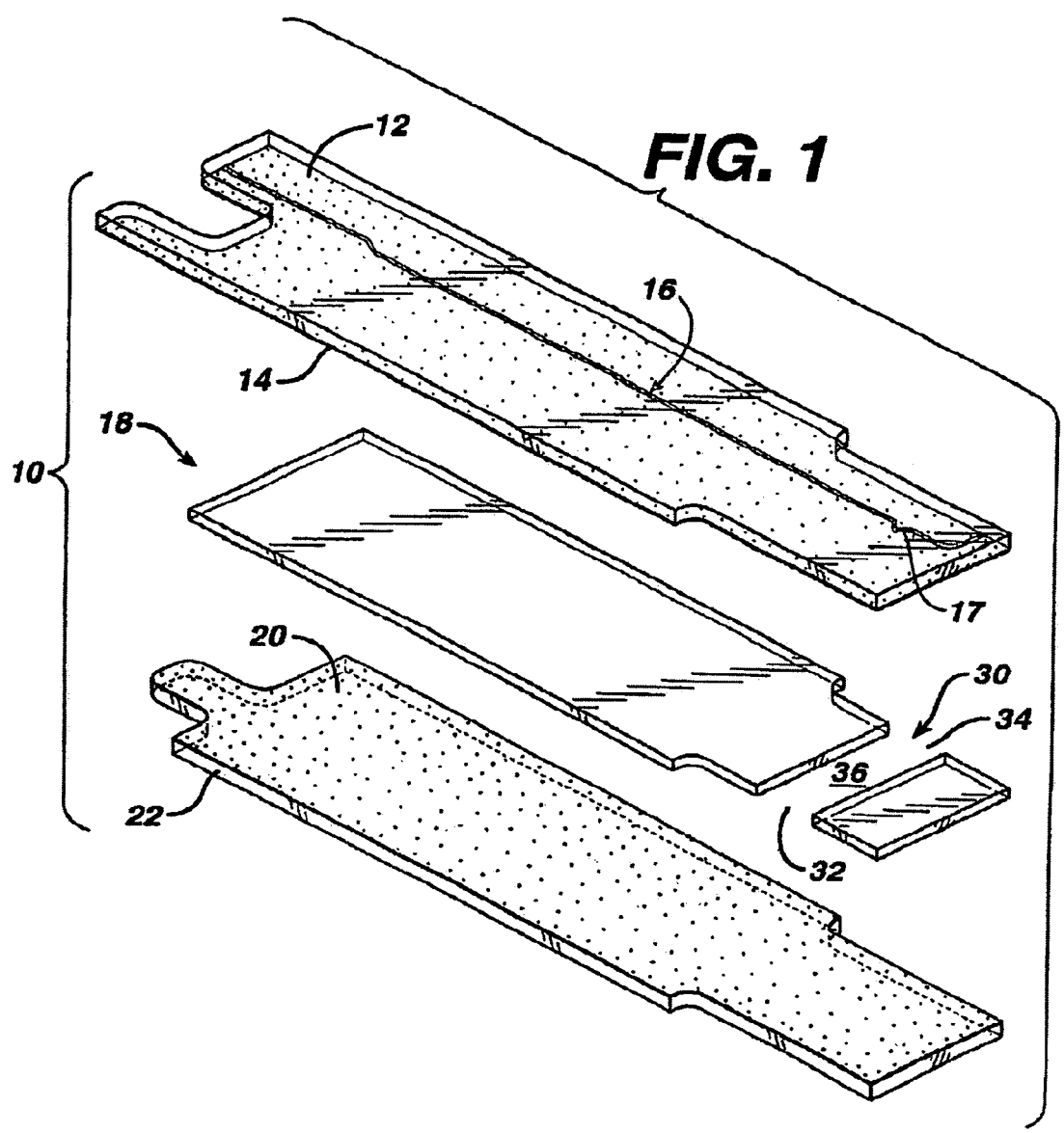
FIG. 1 is an exploded perspective view of a device of the present invention.

FIG. 1 is an exploded view of an embodiment of multilayer device 10. Top insulating sheet 12 has an electrically conductive surface 14, which is typically a metal, plated on a surface of insulating sheet 12 by vacuum deposition, sputtering, electroplating, or any other suitable method for providing a conductive surface, well known in the art. In from a longitudinal edge of surface 14 is scored insulating line 16. Scored line 16 extends through the thickness of surface 14, to provide a gap in the conductive path across the width of the device.

Intermediate insulating layer 18 is sandwiched between conductive surface 14 of top insulating sheet 12 and conductive surface 20 of bottom insulating sheet 22. Intermediate layer 18 is preferably a thermoplastic sheet with adhesive on both surfaces for adhering to sheets 12 and 22. Conductive surface 20 is typically a metal plated on sheet 22 by one of the methods mentioned earlier. Cutout 30 in intermediate layer 18 provides—between conductive-coated sheets 12 and 22—inlet 32, outlet 34, and the electrochemical cell 36 that lies between the inlet and outlet. An optional serration 17 in scored line 16 enhances flow from inlet 32 to outlet 34, by a mechanism that is described later. Within channel 30, a dry reagent, consisting of buffer, mediator, and enzyme, is deposited on conductive surface 20 and/or, 14. Electrochemical cell 36 is the region within which is measured an electrical parameter of the fluid/reagent combination. The region in which the reagent is coated generally, but not necessarily, corresponds to the cell 36. For simplicity, that correspondence is assumed in the description below. The reagent and electrochemical cell 36 may be limited to the region between insulating line 16 and the inlet 32. Alternatively, the reagent coating (and cell) may extend over the entire cutout region between the edges of the device.

Figure 2:
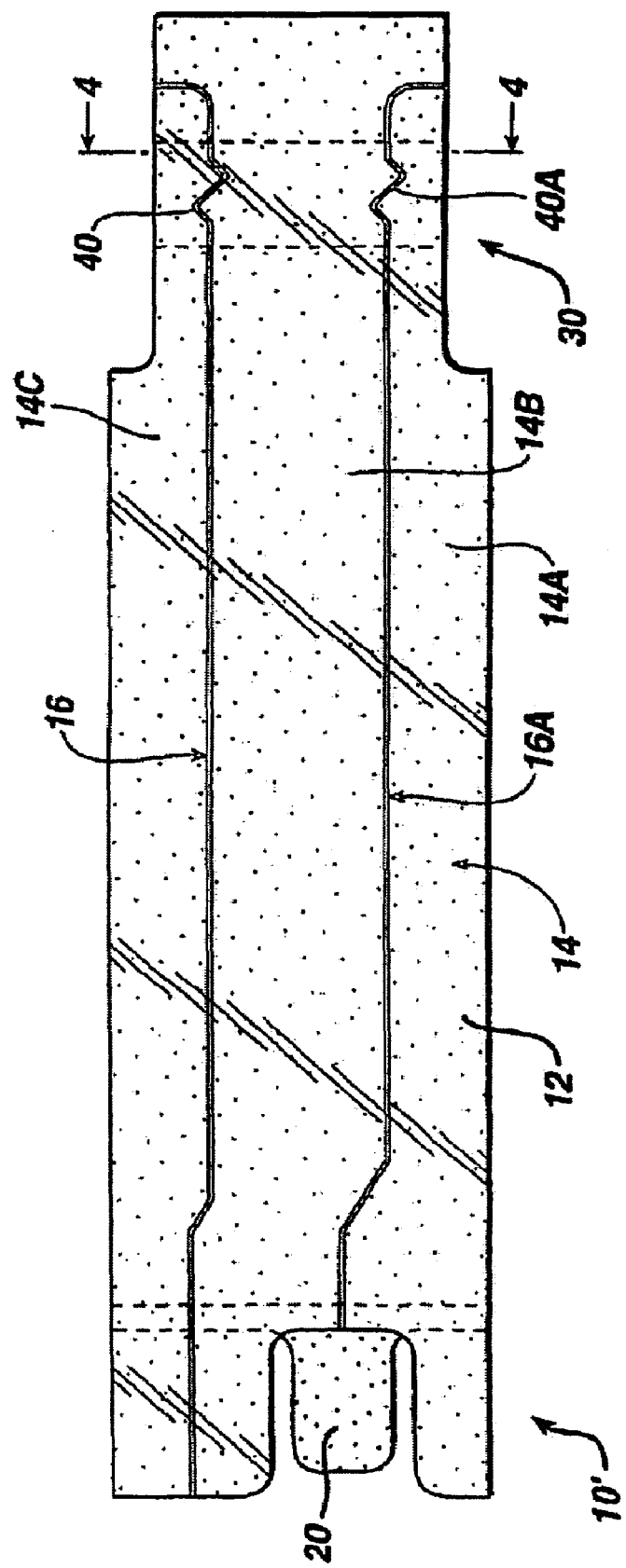
FIG. 2 is a plan view of another device of the present invention.

FIG. 2 is a plan view of another embodiment of the device of FIG. 1. The device 10' of FIG. 2 includes a second scored line 16A, in from the other longitudinal edge of conductive surface 14. Thus, the device of FIG. 2 is symmetrical, so that the sample can be admitted from either edge; i.e., there is no distinction between inlet and outlet. Score lines 16 and 16A divide conductive surface 14 into three regions—14A, 14B, and 14C—each insulated from the other two. As is clear in FIG. 2, score lines 16 and 16A have serrations 40 and 40A, respectively, that form angles, whose vertices "point" to both edges of the device. The serrations are provided to enhance flow through channel 30 in both directions, as described below.

When fluid flows through a capillary channel, such as channel 30, a discontinuity in channel cross section can form a "stop junction," which can stop the fluid flow, as described in U.S. Pat. Nos. 4,426,451; 5,230,866; and 5,912,134, incorporated herein by reference. Score lines 16 and 16A create such cross section discontinuities. The stop junction results from surface tension that creates a back pressure that stops the fluid meniscus from proceeding through the discontinuity. The stop junction is weakened, and flow thereby enhanced, when the leading edge of the meniscus encounters the vertex of an acute angle and is then stretched along the arms of the angle. This may be described as the angle "pointing" in a direction opposite to the direction of fluid flow. This process may be better understood by reference to FIGS. 3A, 3B, and 3C.

Figure 3A:
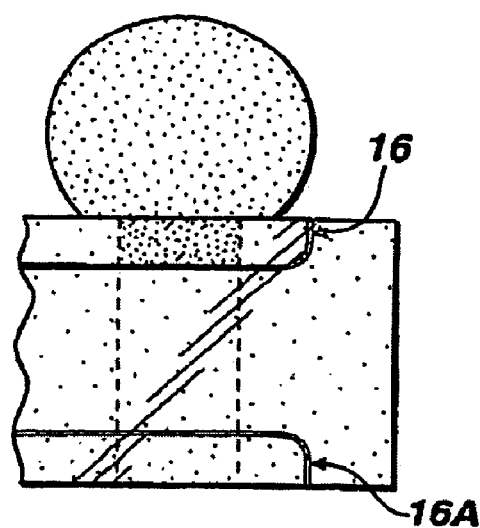
FIG. 3A schematically depicts the operation of a stop junction in stopping fluid flow through a capillary channel.

FIG. 3A depicts the action of the stop junction when the serration is absent. The fluid (flowing left-to-right in the figure) is stopped at score line 16. A serration in score line 16 (such as serration 17 in FIG. 1) serves to weaken the stop junction and facilitates flow through the scored region. Although serration 17 would weaken the stop junction, and thereby facilitate fluid flow in both directions through capillary channel 30, the effect is not the same for both directions.

Figure 3B:
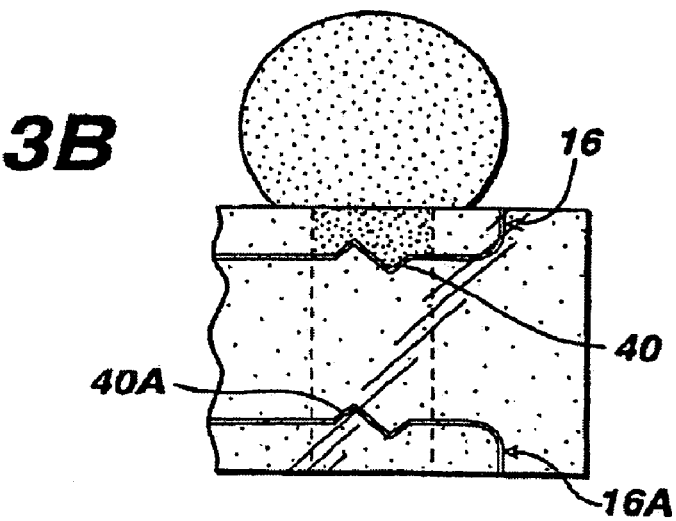
FIGS. 3B, and 3C schematically depict fluid flow through a capillary channel of the device of FIG. 2.
Figure 3C:
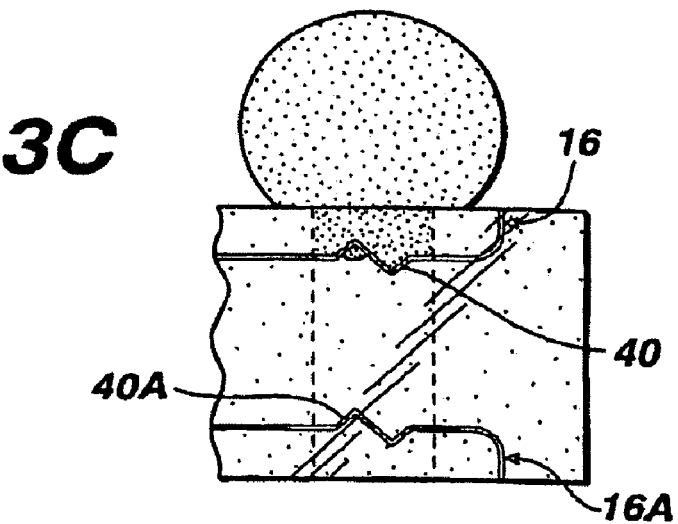

FIGS. 3B and 3C show the fluid before and just after the meniscus breaks through a stop junction having serrations whose vertices point in opposite directions (like that of FIG. 2). Note that the breakthrough occurs first at the vertex that "points" opposite to the direction of fluid flow. The effectiveness of the serration in enhancing flow through a stop junction in a capillary channel depends on the angle and the length of the legs that form the angle. The smaller the angle and the longer the legs, the greater the effectiveness of the serration. Thus, if the angle is small and the legs long, only a small hydraulic pressure differential across the scored region will cause the sample to flow through it.

Figure 4:
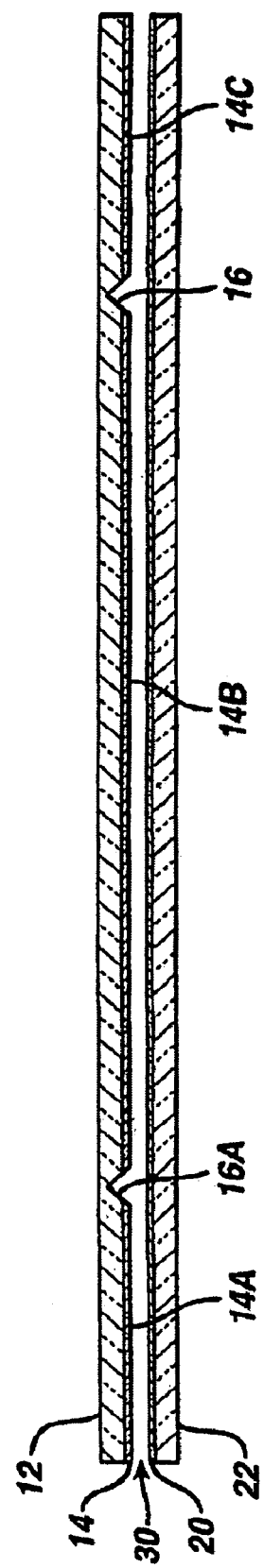
FIG. 4 is a cross-section through the device of FIG. 2.

FIG. 4 is a cross section along the line 4-4 of FIG. 2. As is clear from FIG. 4, score lines 16 and 16A interrupt conductive surface 14 and extend into insulating sheet 12. Conductive surface 14 is typically gold, and conductive surface 20 is typically palladium, but each may alternatively be any other conductive material that does not react with the reagent or sample and that can be applied to an insulating surface. Suitable materials include tin oxide, platinum, iridium, stainless steel, and carbon. The thickness of the coating should at least be sufficient to provide adequate conductivity—generally, about 10 ohms per square, or less. Gold coatings are typically about 10-20 nm, palladium typically about 20-40 nm. The conductive coatings preferably have a hydrophilic overcoating to enhance filling when channel 30 is a capillary channel. The overcoat must adhere to the conductive coating but not react with the sample fluid. Insulating sheets 12 and 22 may be any suitable thermoplastic sheet, such as polyester, polyethylene, polypropylene, polycarbonate, polyimide, etc. Polyester of about 0.2 mm thickness is suitable and inexpensive.

Figure 5:
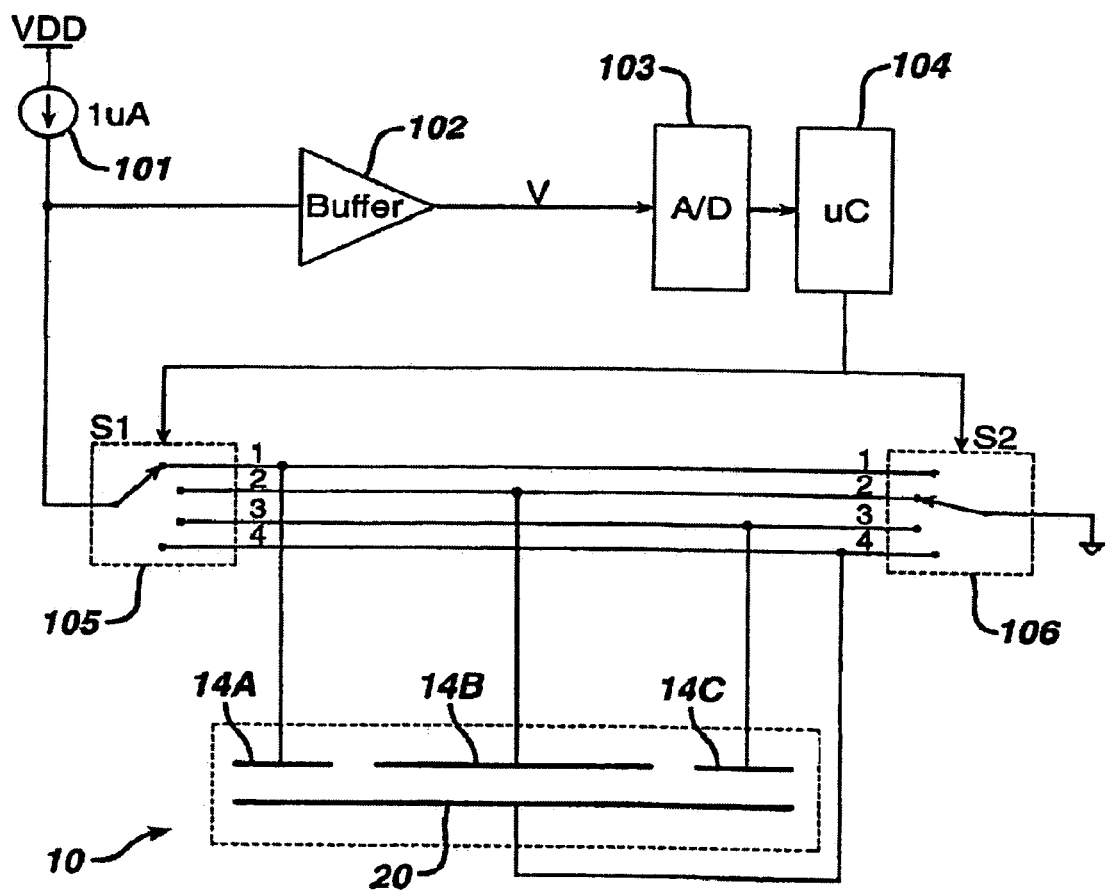
FIG. 5 is a block diagram of a fill-detection circuit of the present invention.

As seen in FIGS. 4 and 5, a fill-detection device 10' of the type shown in FIG. 2 has available four discrete electrodes— 14A, 14B, 14C, and 20. Thus, an electrochemical meter could, in principle, measure the current or voltage output across six different electrode pairs—14A, 20; 14B, 20; 14C, 20; 14A, 14B; 14B, 14C; and 14A, 14C. In a preferred embodiment, a meter periodically (e.g., every 0.1 second) measures the voltages (at constant current) across 14A, 20 and 14C, 20. In that way, the meter detects sample entry and identifies which side of channel 30 the sample is entering. For example, if (conductive) sample enters at the left edge, as shown in FIGS. 4 and 5, voltage 14A, 20 drops. Thereafter, a drop in any of 14A, 14C; 14B, 14C; or 14C, 20 voltages signals that the volume of channel 30 is filled between 16 and 16A. If the time to fill under normal conditions is known, simple error trapping allows a strip to be rejected if fill time exceeds a preset maximum. Similarly, if sample enters at the right edge, voltage 14C, 20 drops, and a drop in 14A, 14C; 14A, 14B, or 14A, 20 signals that channel 30 is filled (at least beyond the serration most distant from the sample entry).

Instead of, or in addition to, monitoring 14A, 20 and 14C, 20 to detect sample entry, 14A, 14B, and 14B, 14C could be monitored to detect partial filling of channel 30. The time at which the cell has filled is determined as described above.

Another alternative for monitoring partial filling is to just measure voltage 14B, 20. That alternative requires less switching and simpler switching controls. By not requiring very rapid switching there may also be a cost saving. The time at which the cell has filled is then signaled by a drop in voltage 14A, 14C. More generally, changes in current or voltage across one or more of the pairs can be used to track the progress of sample into and through the cell. Of course, if only a single score is used (as shown in FIG. 1), there are only three discrete electrodes, and the monitoring options are correspondingly reduced. Inversely, if surface 20 is scored, instead of or in addition to 14, sample flow can be monitored using other, or additional, voltage pairs.

FIG. 5 depicts a block diagram that shows circuitry which can accomplish the fill detection described above. Initially, a constant current source (101) is applied to one of the electrode pair combinations, using switches 105 and 106. With no sample on the strip, the resistances between all six electrode pairs are very large, and the current passing through the strip is negligible. The output voltage of voltage buffer 104(V) is high in this condition. When sample bridges the gap of a monitored pair, the resistance and voltage drop significantly. V then is fed to microcontroller 104 through analog-to-digital converter 103. Microcontroller 104, recognizing this reduced voltage as sample detection, switches 105 and 106 to probe one of the other electrode pairs, to confirm that the cell is filled.

FIG. 6 is an exploded perspective view of an alternative embodiment of a device of this invention, in which sample is applied to the end, rather than side, of the device. Top layer 112 has a coating 114 of a conductor, such as gold, on its underside. The coating has insulating line 116 scored into the surface, and serration 140 in score line 116 facilitates flow of sample into channel 130 of insulating layer 118. Bottom layer 122 has a coating 120 of palladium, or other conductor. Electrical contact with coating 120 is made through access hole 142 in top layer 112 and gap 144 in insulating layer 118. Electrical contact with coating 114 is made through openings 146 in bottom layer 122 and gap 144 in insulating layer 118. Electrochemical cell 136 is formed by channel 130 and the metal-coated top and bottom layers. Note that after the device is assembled, through-hole 148 is punched through all three layers to provide a vent in top layer 112 to permit filling of channel 130 and to provide a stop junction at the distal end of the channel (where hole 148 is cut into insulating layer 118). At the same time, the proximal (open) end of the channel is cut, together with the adjoining ends of layers 112 and 122. The two cuts, made simultaneously in the assembled layers, provide accurate and reproducible channel length, which in turn permits accurate and reproducible measurements.

A device of the type described above can use a glucose oxidase (GOD)/ferricyanide system to determine glucose concentrations via the following reactions, in which GOD* is the reduced enzyme.

glucose+GOD→gluconic acid+GOD*   Reaction 1

GOD*+2ferricyanide→GOD+2ferrocyanide.   Reaction 2

Ferricyanide ($[Fe(CN)_6]^{3-}$) is the mediator, which returns the GOD* to its catalytic state. GOD, an enzyme catalyst, will continue to oxidize glucose so long as excess mediator is present. Ferrocyanide ($[Fe(CN)_6]^{4-}$) is the product of the total reaction. Ideally, there is no ferrocyanide initially, although in practice there is often a small quantity. After the reaction is complete, the concentration of ferrocyanide (measured electrochemically) indicates the initial concentration of glucose. The total reaction, reaction 3, is the sum of reactions 1 and 2.

Reaction 3

glucose + 2ferricyanide $\xrightarrow{GOD}$ gluconic acid + 2ferrocyanide

"Glucose" refers specifically to β-D-glucose.

Details of this system are described in U.S. Pat. No. 5,942, 102, issued on Aug. 24, 1999, and incorporated herein by reference.

A second embodiment of the present invention is a method for providing an electrically-conductive pattern on a conductive-coated flexible insulator, such as sheet 12 of FIG. 2. An apparatus for preparing a pattern such as that designated 16 and 16A in conductive coating 14 is depicted in FIG. 7.

As shown in FIG. 7, web 42, comprising conductive coating 44 on flexible insulator 46 passes between anvil 48 and cutting die 50 to score selected areas of coating 44. The knife regions of die 50 are raised a height h, greater than the thickness of coating 44, so that the cut areas become insulating regions in the coating. However, the knife regions should not be raised so high that the mechanical strength of insulator 46 is undermined. Preferably, the knife height h is about one thousand to ten thousand times the thickness of coating 44, depending on the uniformity and precision of the tooling for cutting. Preferably, as shown, anvil 48 and cutting die 50 are rollers that the web passes between.

Alternative methods for providing a pattern of score lines in a conductive coating will be apparent to a person of ordinary skill in the art. For example, if insulator 46 is deformable, then standard relief patterning methods can be used, such as those used in microreplication. (See, e.g., U.S. Pat. Nos. 5,642,015; 5,514,120; and 5,728,446.)

It will be understood by those skilled in the art that the foregoing descriptions are illustrative of practicing the present invention, but are in no way limiting. Variations of the detail presented herein may be made, without departing from the scope and spirit of the present invention.

We claim:

1. A medical diagnostic device for measuring an analyte concentration of an electrically conductive biological fluid, comprising a multilayer structure having a first layer and a second layer sandwiching an intermediate layer,
   a) the first and second layers each comprising an insulating sheet, having a conductive surface adjoining the intermediate layer,
   b) the intermediate layer being an insulating layer with a cutout, having a first end and a second end, which, together with the first and second layers, defines a capillary channel to permit the sample to flow from the first end to the second end,
   c) the capillary channel comprising
      (i) a dry reagent on the conductive surface of one of the first and second layers for reacting with the sample to yield a change in an electrical parameter that can be related to the analyte concentration of the fluid and
      (ii) an electrochemical cell, within which the electrical parameter is measured,
   d) the conductive surface of one of the first and second layers having a first insulating pattern scored into its conductive surface to divide the conductive surface into two regions, insulated from each other, wherein the first insulating pattern has at least one serration with the capillary channel, whereby sample that flows across the first insulating pattern provides a conductive path from the first end to the second end.

2. The device of claim 1, in which the first end of the cutout is at a first edge of the intermediate layer and the second end is at a second edge of the intermediate layer, opposite the first edge.

3. The device of claim 1, in which the dry reagent is on the conductive surface of the first layer and the insulating pattern is scored into the conductive surface of the second layer.

4. The device of claim 1, in which sample that enters the capillary channel at the first end flows through the electrochemical cell, before it reaches the first insulating pattern.

5. The device of claim 1, in which the biological fluid is blood and the analyte being measured is glucose.

6. The device of claim 1, in which the first and second layers each comprise metallized thermoplastic sheets.

7. The device of claim 1, in which the intermediate layer comprises a thermoplastic sheet having adhesive on both surfaces for adhering to the first and second layers.

8. The device of claim 1, in which the reagent on the conductive surface comprises a buffer, a mediator, and an enzyme.

9. The device of claim 1, wherein the at least one serration is pointing toward each end of the capillary channel.

10. The device of claim 1, further comprising a second insulating pattern scored into the conductive surface of the scored layer between the first end and the first insulating pattern to divide the scored conductive surface into three regions, insulated from each other.

11. The device of claim 10, in which sample that enters the capillary channel at the first end reaches the second insulating pattern before it flows through the electrochemical cell.

12. The device of claim 1, further comprising electrical circuit means for detecting the flow of fluid through the capillary channel.

* * * * *